United States Patent [19]

Ritschel

[11] Patent Number: 4,642,375
[45] Date of Patent: Feb. 10, 1987

[54] PROCESS FOR PREPARING DERIVATIVES OF THE MONOAMIDE OF TEREPHTHALIC ACID

[76] Inventor: Werner Ritschel, Hoechst Aktiengesellschaft P.O. Box 80 03 20, D-6230 Frankfurt am Main 80, Fed. Rep. of Germany

[21] Appl. No.: 790,786

[22] Filed: Oct. 24, 1985

Related U.S. Application Data

[63] Continuation of Ser. No. 553,244, Nov. 18, 1983, abandoned.

[30] Foreign Application Priority Data

Nov. 22, 1982 [DE] Fed. Rep. of Germany ....... 3243148

[51] Int. Cl.$^4$ .............................................. C07C 99/00
[52] U.S. Cl. ..................................... 562/442; 560/37
[58] Field of Search .......................... 562/442; 560/37

[56] References Cited

U.S. PATENT DOCUMENTS

| | | | |
|---|---|---|---|
| 1,991,790 | 2/1935 | Cook et al. | 562/442 |
| 2,798,087 | 7/1957 | Hotten | 560/37 |
| 3,249,636 | 5/1966 | Close | 564/134 |
| 3,252,977 | 5/1966 | Renckhoff et al. | 560/37 |
| 3,288,794 | 11/1966 | Kuceski | 560/37 |
| 3,324,179 | 6/1967 | Scholy et al. | 564/134 |
| 3,931,210 | 1/1976 | Zengel et al. | 562/442 |
| 3,996,265 | 12/1976 | Walker | 560/37 |
| 4,322,551 | 3/1982 | Shah | 564/134 |

OTHER PUBLICATIONS

Rondestvedt, J. Org. Chem., vol. 42, pp. 3118–3123 (1977).

Primary Examiner—James H. Reamer

[57] ABSTRACT

An improved and simplified process for preparing terephthalic acid monoamide derivatives of the formula

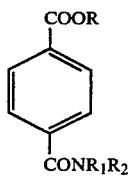

in which R denotes hydrogen, an alkaline earth metal or alkali metal cation or methyl, $R_1$ denotes $C_8$–$C_{30}$-alkyl, preferably $C_{12}$–$C_{22}$-alkyl, and $R_2$ denotes $C_1$–$C_{30}$-alkyl or, preferably hydrogen, in which dimethyl terephthalate is reacted with an amine of the formula $HNR_1R_2$ in methanol and in the presence of sodium methylate. The compounds thus obtained are used for gelling oils and organic solvents.

4 Claims, No Drawings

PROCESS FOR PREPARING DERIVATIVES OF THE MONOAMIDE OF TEREPHTHALIC ACID

This case is a continuation of my copending application Ser. No. 553,244 filed Nov. 18, 1983, now abandoned.

It is known that, in the form of their salts, half-amides of terephthalic acid can gel oils and organic solvents. These gels are used as lubricants. Preparation of these compounds in sufficient purity hitherto required a technically complicated, multistage process in which, first, dimethyl terephthalate is turned into an alkali metal half-salt which is then converted into the half-amide via the acid chloride stage (Ind. and Eng. Chem. 49, (1957) 1691). This process has disadvantages in that not only is the consumption of solvent high, but an auxiliary base has to be used in the reaction of the acid chloride with the amine, which in turn increases costs and leads to problems with the filtering of the hydrochloride.

It is therefore an object of the invention to provide a simplified process for preparing these half-amides of terephthalic acid or methyl esters of these half-amides from dimethyl terephthalate.

Accordingly, the invention relates to a process for preparing terephthalic acid monoamide derivatives of the formula

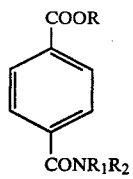

in which R denotes hydrogen, an alkali metal or alkaline earth metal cation or methyl, $R_1$ denotes $C_8$–$C_{30}$-alkyl, preferably $C_{12}$–$C_{22}$-alkyl, and $R_2$ denotes $C_1$–$C_{30}$-alkyl in, preferably, hydrogen, which comprises reacting dimethyl terephthalate with an amine of the formula

in methanol and in the presence of sodium methylate.

It is an essential part of the process according to the invention that methanol is used as a solvent and that sodium methylate is present as a catalyst. Since the ratio of solvent to reactants has a particular effect on the ratio of half-amide to diamide in the end product, it is advisable to take only as much methanol as will ensure that the reaction mixture just remains efficiently stirrable after the half-amide has crystallized out. If too mueh methanol is taken, more terephthalic acid diamide is formed as a by-product. The amount of catalyst has an effect on the duration of the reaction. It is preferable to use an amount of 0.1 to 1 mole of sodium methylate. The reaction lasts about 4 hours in the case of 1 mole of sodium methylate and about 8 hours in the case of 0.5 mole of sodium methylate. The reaction is carried out at the boiling point of methanol. Because of the stoichiometry of the reaction equation, it is preferable to use the two starting compounds in a molar ratio of 1:1.

When the reaction is complete, the precipitated product is conventionally filtered off, washed and dried. As the following examples show, the reaction product additionally contains more or less sizeable proportions of terephthalic acid diamide, depending on the length of the alkyl groups in the amine. These diamides can be separated, if desired, from the half-amides by the customary fractional crystallization methods. However, the mixtures of half-amide and diamide which can be obtained according to the invention are quite adequate for the abovementioned thickening of oils and solvents. Nor does this intended use necessitate separate hydrolysis of the methyl ester which is initially obtained in the reaction described. On the contrary, this ester can be added to the oil or solvent directly and then by hydrolyzed to the alkali metal salt by adding alkali. A prerequisite for this is of course that the oil or solvent itself cannot be hydrolyzed. Alternatively, the methyl ester can of course also be hydrolyzed separately by known methods to give the alkali metal salt. The alkali metal salt can then be turned by similarly known methods into the free acid and salts with other cations.

EXAMPLE 1

19.4 g (0.1 mole) of dimethyl terephthalate in 150 ml of methanol and 0.1 mole of octadecylamine are heated to the reflux temperature, and 18 g (0.1 mole) of sodium methylate (30% strength in methanol) are then rapidly added dropwise. It is observed that, after the addition of $NaOCH_3$, initially the dimethyl terephthalate dissolves completely, only for the product to crystallize out shortly thereafter. The mixture is stirred under reflux for a further 4 hours, and is cooled down to room temperature, and the precipitate is filtered off with suction. The filter cake is then washed, first with methanol and then with water, until the filtrate has a neutral reaction.

This gives 36 g (83.3%) of 4-carbomethoxybenzoic acid octadecylamide having an 11% terephthalic acid bisoctadecylamide content.

Instead of using 18 g of sodium methylate it is also possible to use only 9 g (0.05 mole), but the total refluxing time then has to be 8 hours. This gives a reaction product of the same composition and same quality as above.

EXAMPLE 2

19.4 g (0.1 mole) of dimethyl terephthalate and 18.5 g (0.1 mole) of dodecylamine are refluxed in 100 ml of methanol. After addition of 9 g (0.05 mole) of sodim methylate (30% strength in methanol) refluxing is continued for 8 hours, and the reaction batch is then worked up as described in Example 1, affording 31.7 g (91.2%) of 4-carbomethoxybenzoic acid dodecylamide having a 14% terephthalic acid bisdodecylamide content.

EXAMPLE 3

19.4 g (0.1 mole) of dimethyl terephthalate and 12.9 g (0.1 mole) of octylamine are refluxed for 8 hours in 100 ml of methanol together with 9 g (0.05 mole) of sodium methylate (30% strength). Working up as in Example 1 produces 26.5 g (91%) of 4-carbomethoxybenzoic acid octylamide having a 30% terephthalic acid bisoctylamide content.

The terephthalic acid bisamide content was determined by 1H-NMR spectroscopy in all cases.

I claim:

1. A process for preparing terephthalic acid monoamide derivatives of the formula

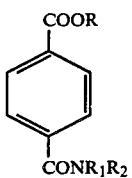

in which R denotes hydrogen, an alkaline earth metal or alkali metal cation or methyl, $R_1$ denotes $C_8-C_{30}$-alkyl, and $R_2$ denotes hydrogen or $C_1-C_{30}$-alkyl, which comprises reacting dimethyl terephthalate with an amine of the formula $HNR_1R_2$ in an approximately 1:1 molar ratio of dimethylterephthalate to said amine, essentially in about 1000 to about 1500 ml of methanol per mole of dimethylterephthalate, at the boiling point of methanol, in the presence of sodium methylate.

2. A process according to claim 1 wherein, in said terephthalic acid monoamide derivative, R denotes methyl.

3. A process according to claim 1 wherein, in said terephthalic acid monoamide derivative, R denotes an alkaline earth metal or alkali metal cation or hydrogen, said derivative having been obtained by hydrolysis from the corresponding terephthalic acid monoamide, monomethyl ester derivative initially obtained as the product of said process.

4. A process according to claim 1, wherein about 0.1 to 1 mole of sodium methylate, as a 30% solution in methanol is combined with the said amounts of dimethylterephthalate, said amine and said methanol.

* * * * *